US00PP13405P3

(12) United States Plant Patent
Danziger

(10) Patent No.: US PP13,405 P3
(45) Date of Patent: Dec. 24, 2002

(54) PETUNIA NAMED 'DANCASPURSPARK'

(75) Inventor: Gabriel Danziger, Nir-Zvi (IL)

(73) Assignee: Danziger "Dan" Flower Farm, Post Beit Dagan (IL)

( * ) Notice: Subject to any disclaimer, the term of this patent is extended or adjusted under 35 U.S.C. 154(b) by 0 days.

(21) Appl. No.: 09/838,230

(22) Filed: Apr. 20, 2001

(65) Prior Publication Data

US 2002/0157160 P1 Oct. 24, 2002

(51) Int. Cl.[7] ..... A01H 5/00

(52) U.S. Cl. ..... Plt./356

(58) Field of Search ..... Plt./356

*Primary Examiner*—Bruce R. Campell
*Assistant Examiner*—Annette H. Para
(74) *Attorney, Agent, or Firm*—Foley & Lardner

(57) ABSTRACT

A new and distinct cultivar of petunia plant named 'Dancasoft', as described and illustrated, and particularly characterized by the combined features of pale purple flower color with vibrant purple veins, single flower type, early year round flowering time, medium flower size, spreading, well branched, vigorous growth habit, very floriferous, long bloom season, good weather tolerance, suitable for hanging baskets and mass covering.

1 Drawing Sheet

BACKGROUND OF THE INVENTION

Latin name of the genus and species of the claimed plant: *Petunia hybrida.*

Variety denomination: Dancaspurspark.

The present invention comprises a new and distinct cultivar of petunia, known by the cultivar name 'Dancaspurspark'. 'Dancapurspark' originated from a hybridization made by the inventor in a controlled breeding program in Mishmar Hashiva, Israel in 1999. The female was 'Pink Spark', U.S. Plant Pat. No. 10,857. The male parent of 'Dancaspurspark' was 'CV. 4021' (unpatented).

'Dancaspurspark' was discovered and selected as one flowering plant within the progeny of the stated cross by or under the supervision of the inventor Gabriel Danziger in May, 1999, in a controlled environment in Mishmar Hashiva, Israel.

The first act of asexual reproduction of 'Dancaspurspark', was accomplished when vegetative cuttings were taken from the initial selection in June 1999 in a controlled environment in Mishmar Hashiva, Israel by a technician working under formulations established and supervised by the inventor.

Horticultural examination of selected units initiated September, 1999, has demonstrated that the combination of characteristics as herein disclosed for 'Dancaspurspark' are firmly fixed and are retained through successive generations of asexual reproduction.

'Dancaspurspark' has not been observed under all possible environmental conditions. The phenotype may vary somewhat with variations in environment such as temperature, light intensity and day length, however, without any variations in genotype. The following observations, measurements and comparisons describe the plants grown in Mishmar Hashiva, Israel, under greenhouse conditions which approximate those generally used in commercial practice.

BRIEF DESCRIPTION OF THE INVENTION

The following traits have been repeatedly observed and are determined to be basic characteristics of 'Dancaspurspark' which in combination distinguish this petunia as a new and distinct cultivar:

1. Pale purple flower color and vibrant purple veins;
2. Single flower type;
3. Early year round flowering time;
4. Medium flower size;
5. Spreading, well branched, vigorous growth habit, very floriferous, long bloom season;
6. Good weather tolerance; and
7. Suitable for hanging baskets and mass covering.

Of the many commercial cultivars known to the present Inventor (s), the most similar in comparison to 'Dancaspurspark' is 'Pink Spark' by Danziger. In comparison to Pink Spark, 'Dancaspurspark' has bigger flowers, is more floriferous, has better branching, is more trailing, has earlier flowering, and with darker shades and more brilliant flower color.

BRIEF DESCRIPTION OF THE DRAWING

The accompanying photographic drawing(s) show typical flower and foliage characteristics of 'Dancaspurspark', with the color being as true as possible with illustrations of this type.

DETAILED BOTANICAL DESCRIPTION

In the following description color references are made to The Royal Horticultural Society Colour Chart. The color values were determined between 10:00 a.m. and 12:00 p.m. in October, 2000, under full sunlight at Mishmar Hashiva, Israel.

Plant:

*Age.*—3 months.
*Growth habit.*—Trailing vigorously.
*Plant height.*—6–8 inches.
*Spreading area.*—30 inches.
*Blooming period.*—All year round in moderate climate.

Stem:

*Thickness.*—4 mm.
*Color.*—Green RHS 143B.

*Pubescence*.—Yes.
*Branching*.—Freely.
*Internode length*.—10–20 mm.

Leaf:
*Arrangement on stem*.—Alternate.
*Shape*.—Elliptic.
*Apex*.—Acuminate.
*Base*.—Rounded.
*Margin*.—Entire.
*Venation*.—None.
*Size*.—Length: 70 mm. Width: 35 mm.
*Thickness*.—0.2 mm.
*Color*.—Green RHS 137 C both surfaces.
*Markings*.—None.
*Pubescence*.—Yes.

Flower:
*Flower longevity*.—5–7 days.
*Fragrance*.—None.
*Orientation at opening*.—Upright.
*Type*.—Single.
*Shape*.—Regular, rounded, corolla united with 5 lobes and a long straight tube.
*Diameter*.—55 mm.
*Petals*.—Number: 5 lobes united. Shape: Salver form. Size: 4.5 cm in length, 6 cm in width. Apex: Truncate. Margin: Entire. Texture: Smooth. Color: Violet, RHS 88 C (both surfaces); with red-purple veins, RHS 71 A.
*Sepals*.—Number: 5. Shape: Oblong. Size: 15 mm in length, 2 mm in width. Apex: Acuminate. Margin: Entire. Texture: Pubescent. Color: Green, RHS 143 B both surfaces.
*Bud*.—Shape: Oblong. Length: 4 cm. Diameter: 8 mm. Color: Violet, RHS 83 B.
*Peduncle*.—Length: 10–15 mm. Color: Yellow-green RHS 144 B.

Reproductive organs:
*Pistil*.—1, color violet RHS 86 C, 20 mm in length.
*Stigma*.—2 lobed, violet RHS 83 D.
*Style*.—17 mm in length.
*Ovary*.—Yellow-green RHS 144 B.
*Stamen*.—5.
*Anther*.—Violet-blue RHS 92 A.
*Filament*.—Violet-blue RHS 92 D.
*Pollen*.—RHS 92 A, amount unquantifiable.
*Fruit*.—Number: Ten. Shape: Ovate. Size: 8 mm in length, 4 mm in diameter. Color: Greyed-orange, RHS 177 B.
*Seed*.—Number: 40–50. Shape: Rounded. Size: 1 mm in length, 1 mm in diameter. Color: Greyed-orange, RHS 165 A.

Weather resistance: Relatively high rain, heat, and drought resistance.

Disease/pest resistance: Unknown.

I claim:

1. A new and distinct cultivar of petunia plant named 'Dancaspurspark', as described and illustrated.

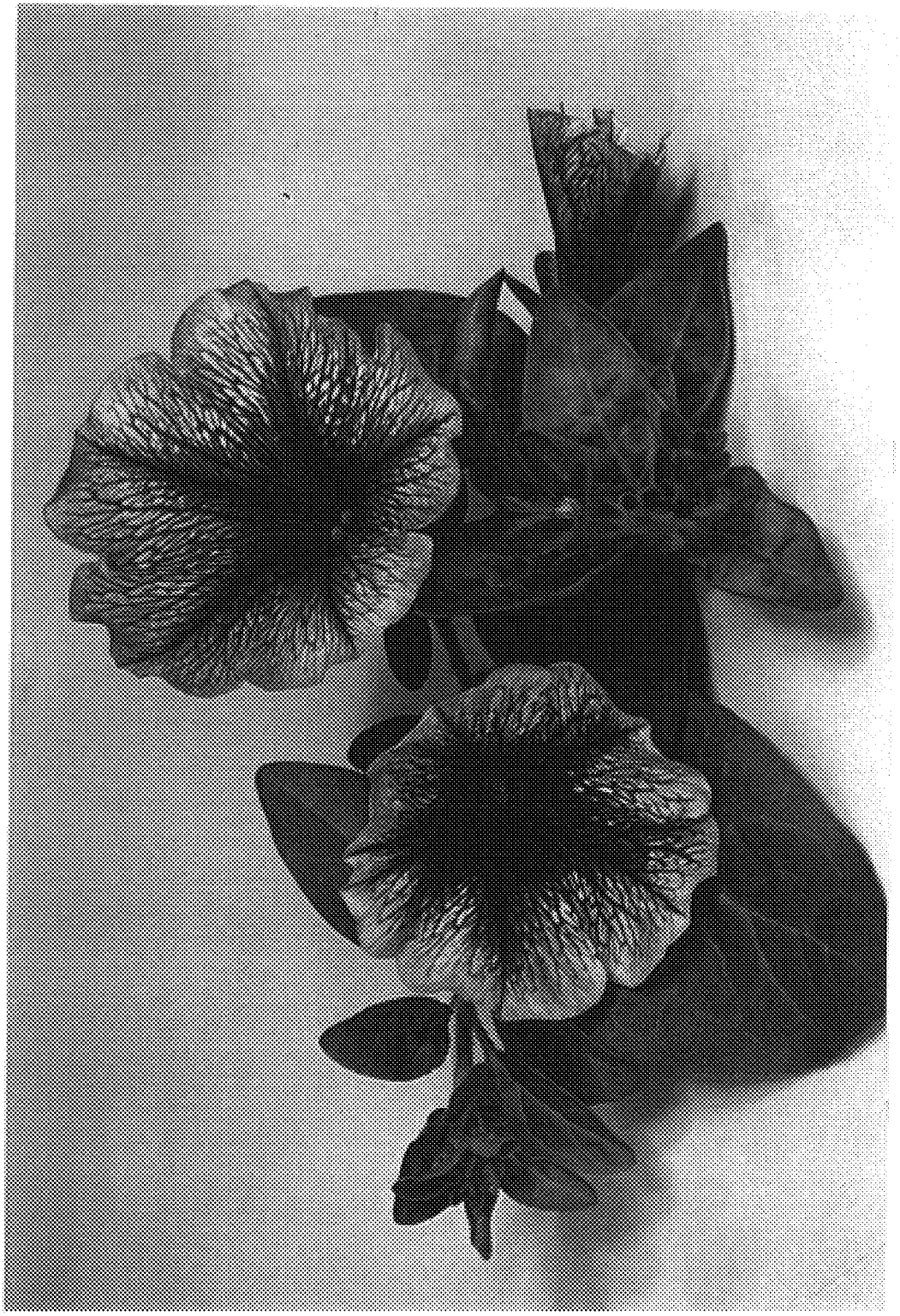

* * * * *